(12) United States Patent
Mohammadrezazadeh et al.

(10) Patent No.: US 10,775,887 B2
(45) Date of Patent: Sep. 15, 2020

(54) NEURO-ADAPTIVE BODY SENSING FOR USER STATES FRAMEWORK (NABSUS)

(71) Applicant: HRL Laboratories, LLC, Malibu, CA (US)

(72) Inventors: Iman Mohammadrezazadeh, Los Angeles, CA (US); Rajan Bhattacharyya, Sherman Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 16/252,247

(22) Filed: Jan. 18, 2019

(65) Prior Publication Data
US 2019/0227626 A1    Jul. 25, 2019

Related U.S. Application Data

(60) Provisional application No. 62/620,357, filed on Jan. 22, 2018, provisional application No. 62/767,276, filed on Nov. 14, 2018.

(51) Int. Cl.
*A61B 5/04*     (2006.01)
*G06F 3/01*     (2006.01)
(Continued)

(52) U.S. Cl.
CPC ............ *G06F 3/015* (2013.01); *A61B 5/0476* (2013.01); *A61B 5/165* (2013.01); *A61B 5/7275* (2013.01); *A61N 1/36031* (2017.08); *G06N 20/00* (2019.01)

(58) Field of Classification Search
CPC .. A61B 5/16; A61B 5/165; A61B 5/02; A61B 5/0205; A61B 5/02055;
(Continued)

(56) References Cited

U.S. PATENT DOCUMENTS 8,396,249 B1 *  3/2013  Khosla ................ G06K 9/3241
                                                        382/103
8,483,816 B1 *  7/2013  Payton .................... G06F 3/015
                                                        600/544
(Continued)

FOREIGN PATENT DOCUMENTS

WO    WO2015-127361 A1    8/2015

OTHER PUBLICATIONS

Borghini, F. (2017). EEG-based cognitive control behaviour assessment: an ecological study with professional air traffic controllers. Nature. Scientific Reports, 7: 547, pp. 1-16.
(Continued)

*Primary Examiner* — Michael J Eurice
(74) *Attorney, Agent, or Firm* — Tope-McKay & Associates

(57) ABSTRACT

Described is a system for personalizing a human-machine interface (HMI) device based on a mental and physical state of a user. During performance of a task in a simulation environment, the system extracts biometric features from data collected from body sensors, and extracts brain entropy features from electroencephalogram (EEG) signals. The brain entropy features are correlated with the biometric features to generate a mental-state model. The mental-state model is deployed in a HMI device during performance of the task in an operational environment for continuous adaptation of the HMI device to its user's mental and physical states.

17 Claims, 13 Drawing Sheets

(51) Int. Cl.
| | |
|---|---|
| *G06N 20/00* | (2019.01) |
| *A61N 1/36* | (2006.01) |
| *A61B 5/0476* | (2006.01) |
| *A61B 5/00* | (2006.01) |
| *A61B 5/16* | (2006.01) |

(58) Field of Classification Search
CPC . A61B 5/024; A61B 5/02416; A61B 5/02405; A61B 5/02438; A61B 5/0245; A61B 5/04001; A61B 5/04012; A61B 5/0402; A61B 5/0476; A61B 5/4809; A61B 5/4812; A61B 5/4824; A61B 5/486; A61B 5/0488; A61B 5/053; A61B 5/0531; A61B 5/0533; A61B 5/0006; A61B 5/6804; A61B 5/681; A61B 5/6803; A61B 5/6805; A61B 5/6829; A61B 5/6831; A61B 5/7221; A61B 5/7246; A61B 5/726; A61B 5/7264; A61B 5/7275; A61B 5/7282; A61B 5/7285; A61B 5/746; A61B 5/0816; A61B 2560/0223; G06F 1/163; G06F 3/015; G06F 19/30; G06F 21/32
See application file for complete search history.

(56) References Cited

U.S. PATENT DOCUMENTS

| | | | | |
|---|---|---|---|---|
| 9,445,739 | B1* | 9/2016 | Payton | A61B 5/0476 |
| 9,824,607 | B1* | 11/2017 | Bhattacharyya | G06F 3/015 |
| 2010/0076333 | A9* | 3/2010 | Burton | A61B 5/0476 600/544 |
| 2011/0288379 | A1 | 11/2011 | Wu | |
| 2014/0276549 | A1* | 9/2014 | Osorio | A61M 5/1723 604/503 |
| 2015/0182130 | A1* | 7/2015 | Utter, II | A61B 5/0205 600/483 |
| 2015/0186609 | A1* | 7/2015 | Utter, II | A61B 5/0022 600/301 |
| 2016/0073914 | A1* | 3/2016 | Lapetina | A61B 5/6824 600/384 |
| 2016/0095527 | A1* | 4/2016 | Thng | A61B 5/6808 600/301 |
| 2016/0103487 | A1* | 4/2016 | Crawford | G06F 3/015 600/544 |
| 2016/0262670 | A1* | 9/2016 | Wasson | A61B 5/14503 |
| 2016/0374588 | A1* | 12/2016 | Shariff | A61B 5/7475 600/547 |
| 2017/0000415 | A1* | 1/2017 | Lapetina | A61B 5/0006 |
| 2017/0011210 | A1* | 1/2017 | Cheong | A61B 5/0022 |
| 2017/0014037 | A1* | 1/2017 | Coppola | A61B 5/044 |
| 2017/0095674 | A1* | 4/2017 | Hresko | A61N 1/3993 |
| 2017/0120107 | A1* | 5/2017 | Wisbey | G09B 19/00 |
| 2017/0131768 | A1 | 5/2017 | Budavari et al. | |
| 2017/0228512 | A1* | 8/2017 | Driscoll | G06F 19/3418 |
| 2017/0281086 | A1 | 10/2017 | Donaldson | |
| 2017/0296048 | A1 | 10/2017 | Lahiri et al. | |
| 2018/0168464 | A1* | 6/2018 | Barnett, Jr. | A61B 5/02055 |
| 2018/0185662 | A1* | 7/2018 | Foshee, Jr. | A61B 5/4836 |
| 2019/0091403 | A1* | 3/2019 | Osorio | A61B 5/0205 |
| 2019/0183412 | A1* | 6/2019 | Huijbregts | A61B 5/486 |
| 2019/0314600 | A1* | 10/2019 | Patel | A61B 5/0478 |

OTHER PUBLICATIONS

Findlater and McGrenere (2004). A comparison of static, adaptive, and adaptable menus, CHI, 2004 Proceedings of the SIGCHI Conference on Human Factors in Computing Systems, pp. 89-96.

Benson, J. (2015). Natick scientists investigate ways to help soldiers recover from stress. Natick Soldier Research, Development and Engineering Center (NSRDEC) Public Affairs, pp. 1-3.

Lebedev, M. (2011). Future developments in brain-machine interface research. Clinics (Sao Paulo), 66(Suppl 1): pp. 25-32.

Luque-Casado, A., Zabala, M., Morales, E., Mateo-March, M., Sanabria, D. (2013). Cognitive Performance and Heart Rate Variability: The Influence of Fitness Level. PLoS ONE, 8(2), pp. 1-9.

Hogervorst, M.A., Brouwer, A.M. and van Erp, J.B.F. (2014). Combining and comparing EEG, peripheral physiology and eye-related measures for the assessment of mental workload. Front. Neurosci., Oct. 14, 2014, pp. 1-14.

Picard, R.W. Detecting seizures and their autonomic impact with a wristband. MIT, 2012, pp. 1-5.

Optimizing Human-Automation Team Workload through a Non-Invasive Detection System. DARPA—Office of the Under Secretary of Defense for Acquisition, 2016, pp. 1-12.

IARPA—Using Neural Tools to Augment Prediction of Performance, Expertise, and Domain-knowledge, 2014, pp. 1-5.

Marcora, Staiano, and Manning V. (2008). Mental fatigue impairs physical performance in humans. Journal of Applied Physiology Published Mar. 1, 2009, vol. 106 No. 3, pp. 857-864.

Yang, Fang, Sun, Siemionow, et al. (2009). Weakening of Functional Corticomuscular Coupling during Muscle Fatigue. Brain Res., 1250: pp. 101-112.

Zimmer, H. (2002). Habituation and recovery of a slow negative wave of the event-related brain potential. International Journal of Psychophysiology, vol. 43, pp. 225-235, 2002.

Gawron, V.J. (2000). Human performance measures handbook. Mahwah, NJ, US: Lawrence Erlbaum Associates Publishers, Section 3, Subjective Measures of Workload, section 3.2, pp. 102-152.

Chandra, Verma, Sharma, Mittal, and Jha (2015). EEG based cognitive workload classification during NASA MATB-II multitasking. International Journal of Cognitive Research in Science, Engineering and Education. vol. 3, No. 1, pp. 35-42.

Bossard, Kermarrec, Buche, and Tisseau (2008). Transfer of learning in virtual environments: a new challenge? Virtual Reality, vol. 12, Issue 3, pp. 151-161.

Mohammad-Rezazadeh, Firoozabadi, Hashemi, Hu (2011). A Novel Human-Machine Interface based on Recognition of Multi-Channel Facial Bioelectric Signals. Australas Phys Eng Sci Med, 34: pp. 497-513.

Mohammad-Rezazadeh, Firoozabadi, Hu, Hashemi Golpayegani (2012). Co-Adaptive and Affective Human-Machine Interface for Improving Training Performances of Virtual Myoelectric Forearm Prosthesis. IEEE Transactions on Affective Computing, vol. 3: pp. 285-297.

Castanedo, F. (2013). A Review of Data Fusion Techniques. The Scientific World Journal. vol. 2013, Article ID 704504, pp. 1-20.

Fallahi, M., Heidarimoghadam, R., Motamedzade, M., Farhadian, M. (2016). Psycho Physiological and Subjective Responses to Mental Workload Levels during N-Back Task. J Ergonomics, 6:181, pp. 1-7.

Kolouri, S., Park, S., Thorpe, M., Slepcev, D. and Rohde, G.K. (2017). Optimal Mass Transport: Signal Processing and Machine-Learning Applications. IEEE Signal Process Mag., 34(4): pp. 43-59.

Kumar, N., Kumar J. (2016). Measurement of Cognitive Load in HCI Systems Using EEG Power Spectrum: An Experimental Study. Procedia Computer Science, 84: pp. 70-78.

Notification of Transmittal of International Search Report and the Written Opinion of the International Searching Authority for PCT/US2019/014322; dated Apr. 29, 2019.

International Search Report of the International Searching Authority for PCT/US2019/014322; dated Apr. 29, 2019.

Written Opinion of the International Searching Authority for PCT/US2019/014322; dated Apr. 29, 2019.

* cited by examiner

| Method | Limitation |
|---|---|
| Questionnaires (NASA TLX) | • Subjectively biased to performance when used understand some forms of dynamic information in user's cognitive and emotional states. |
| Bio-signals (EEG from the brain, heart, skin resistance, muscles, and pupil. | • Mostly in laboratory environments, researchers have used EEG signals to control HMIs and also extract user's mental states [Lit. Ref. Nos. 1 and 3]. However EEG collection, even with using current state-of-art "easy-cap" and dry electrodes technologies, is not convenient for users who do not appreciate wearing EEG caps (usability factor).<br>• Extraction of useful EEG feature in operational contexts sometimes requires extensive data cleaning and pre-processing steps [Lit. Ref. No. 4].<br>• HRV and GSR have been also used to detect mental, cognitive and physical states such as stress and physical activity, respectively [Lit. Ref. Nos. 5,6,7]; However, there is limitation in the accuracy of using those signals because different cognitive states in different contexts may produce similar HRV/GSR which make it difficult to discriminate different level of cognitive workload.<br>• Despite rich information content in other bio-signals (such as HRV and GSR), their fusion with EEG has NOT been employed and thus current designs in EEG-based HMI such as one proposed by ARL-HRED [Lit. Ref. No. 3] suffer from lacking of a universal and robust feature (in case of degraded EEG quality), especially in dynamic contexts. |

FIG. 9
(Prior Art)

| Prior Art | Limitation |
|---|---|
| Brain states related to clinical disorders such as epilepsy can be detected using GSR. | Application and processing do not address building a universal mental state model and is limited to certain environmental conditions. |
| Correlations between EEG, HRV, and GSR exist | Done in laboratory conditions with predefined stimuli (not interactive, continuous tasks) |
| Stress can be measured in training operations through multimodal sensing | Still relying on utilizing intrusive sensors (EEG). Not fieldable for operations, only training. |

FIG. 10
(Prior Art)

| Novelty | Current SOA | NABSUS |
|---|---|---|
| Continuous Performance Predictor | Recent studies utilize linear modeling approach or linear features which cannot cope with both the complexity of data as well as nonlinearity between workload and performance [Lit. Ref. No. 12]. Thus, they cannot be used over long period of time and they need recalibration which makes them less useful in applications in daily life. | The invention is the first of its kind which will generate a time-variable and dynamic model of HMI's user by employing subjective and objective performance indices (scores), and biosignals. The method will enhance partnering skills for Human Machine Symbiosis. |
| Generalized User Model : Testing in Different Contexts | Current SOAs [Lit. Ref. No. 13] mostly are validated on unrealistic and desktop tasks (such as NASA MATB-II) which makes it hard to transfer an obtained user model to different working context. | In the invention, the approach was tested in a virtual environment (VE) which is more naturalistic and able to capture commonalities of behavior and brain states in a more naturalistic setting [Lit. Ref. No. 14]. Thus, user model is more generalizable, robust and transferable to naive tasks and conditions. |

FIG. 11
(Prior Art)

NEURO-ADAPTIVE BODY SENSING FOR USER STATES FRAMEWORK (NABSUS)

CROSS-REFERENCE TO RELATED APPLICATIONS

This is a Non-Provisional Application of U.S. Provisional Application No. 62/620,357, filed in the United States on Jan. 22, 2018, entitled, "Neuro-Adaptive Body Sensing for User States Framework (NABSUS)," the entirety of which is incorporated herein by reference.

The present application is ALSO a Non-Provisional Application of U.S. Provisional Application No. 62/767,276, filed in the United States on Nov. 14, 2018, entitled, "Neuro-Adaptive Body Sensing for User States Framework (NABSUS)," the entirety of which is incorporated herein by reference.

BACKGROUND OF INVENTION

(1) Field of Invention

The present invention relates to a system for personalizing a human-machine interface device and, more particularly, to a system for personalizing a human-machine interface device that utilizes bio-signals from a user for its adaptation to the user.

(2) Description of Related Art

Currently, there are no reliable tools able to assess at which level of cognitive control an operator/user is dealing with in a human-machine interface (HMI) (see the Literature of Reference No. 1 of the List of Incorporated Literature References). An HMI is a component of a device (e.g., sensors attached to users, processing unit to extract useful information, display to show output to users) that is capable of handling human-machine interactions. The interface consists of hardware and software that allows user inputs to be translated as signals for machines that provide the required result to the user.

Some HMI designs have utilized questionnaires, such as the NASA task load index (NASA-TLX) which is a subjective, multi-dimensional assessment tool that rates perceived workload in order to assess a task, system, user, or team's effectiveness or other aspects of performance. Using questionnaires, such as NASA TLX, in HMI design are argued to be inadequate to understand some forms of dynamic information in user's cognitive and emotional states.

Researchers have also used electroencephalogram (EEG) signals to control HMIs and extract user's mental states (see Literature Reference Nos. 1 and 3). However EEG collection, even when using current state-of-the-art "easy-cap" and dry electrodes technologies, is not convenient for users who do not appreciate wearing EEG caps (usability factor). Furthermore, current HMI are context-dependent and the interface is not generalizable to other operational contexts. Extraction of useful EEG features in operational contexts sometimes requires extensive data cleaning and pre-processing steps and mostly relies on event-related potential (ERP) signals, not continuous recording of EEG (see Literature Reference No. 4).

In addition, heart rate variability (HRV) sensors and galvanic skin response (GSR) sensors have been used to detect mental, cognitive, and physical states, such as stress and physical activity (see Literature Reference Nos. 5, 6, and 7). However, there are limitations in the accuracy of using those signals because different cognitive states in different contexts may produce similar HRV/GSR outputs, which make it difficult to discriminate different levels of cognitive workload.

Despite rich information content in bio-signals (such as HRV and GSR), their fusion with EEG has not been employed and, thus, current designs in EEG-based HMI, such as one proposed by ARL-HRED (see Literature Reference No. 3) suffer from lack of a universal and robust feature (in the case of degraded EEG quality), especially in dynamic contexts. Most state-of-the-art studies have only been tested in laboratory environments and not in operational fields. Further, the studies are very limited to work under certain conditions, such as high signal to noise ratio for EEG signals, which is not practical in operational situations. For example, it is not practical to ask soldiers in battlefields to wear an EEG headset (even with few electrodes), since the headsets are heavy and very susceptible to noises (e.g., motion artifacts). The state-of-the-art currently lacks capacity to personalize a user-centered HMI.

Recently, many studies have been done to detect the user's state by developing non-invasive and wearable technologies using different forms of bio-signals (signals from brain, heart, muscles, and pupils). However, most of the HMIs are static (see Literature Reference No. 2) and force the users to adapt themselves to variations in operational situations without considering the users' cognitive/mental state. This lack of adaptability in different operational conditions (i.e., deteriorated conditions such as working under stress for rapid task execution, or extreme changes in the operational situations) limits the performance in a human-in-the-loop system. In other words, the machine doesn't utilize extracted bio-signals/states for its adaptation to the user and current context. The lack of interface adaptability in different operational conditions (i.e., deteriorated conditions such as working under stress for rapid task execution, or extreme changes in the operational situations) is one of the most important issues in previous research in the HMI area.

Thus, a continuing need exists for an advanced personalized HMI that can utilize extracted bio-signals from a user for its adaptation to the user and the current situation or application environment.

SUMMARY OF INVENTION

The present invention relates to a system for personalizing a human-machine interface device, and more particularly, to a system for personalizing a human-machine interface device that utilizes bio-signals from a user for its adaptation to the user. The system comprises one or more processors and a non-transitory computer-readable medium having executable instructions encoded thereon such that when executed, the one or more processors perform multiple operations. During performance of a task in a simulation environment, the system extracts a first set of biometric features from data collected from one or more body sensors; and a set of brain entropy features from electroencephalogram (EEG) signals. The set of brain entropy features are correlated with the first set of biometric features, resulting in a correlation of features. A mental-state model is generated as a function of the correlation of features. The mental-state model is deployed in a HMI device during performance of the task in an operational environment for continuous adaptation of the HMI device to its user's mental and physical states.

In another aspect, during performance of the task in the operational environment, the deployed mental-state model is used to predict a mental state.

In another aspect, during performance of the task in the operational environment, the system extracts a second set of biometric features from data collected from the one or more body sensors, and refines the deployed mental-state model with the second set of biometric features, resulting in a refined mental-state model.

In another aspect, the system controls application of neurostimulation during performance of the task in the operational environment based on the refined mental-state model.

In another aspect, in generating the mental-state model, the set of brain entropy features are further correlated with a set of performance metrics, wherein the set of performance metrics are obtained during the task performance in the simulation environment.

In another aspect, in generating the mental-state model, the set of brain entropy features are further correlated with a set of environmental condition features.

In another aspect, human inputs are translated into commands for the HMI deploying the mental-state model.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 9 is a table illustrating limitations of previous methods according to prior art;

FIG. 10 is a table illustrating limitations of previous methods according to prior art;

FIG. 11 is a table illustrating a comparison between current state-of-the art and the method according to prior art;

DETAILED DESCRIPTION

Figure 1:
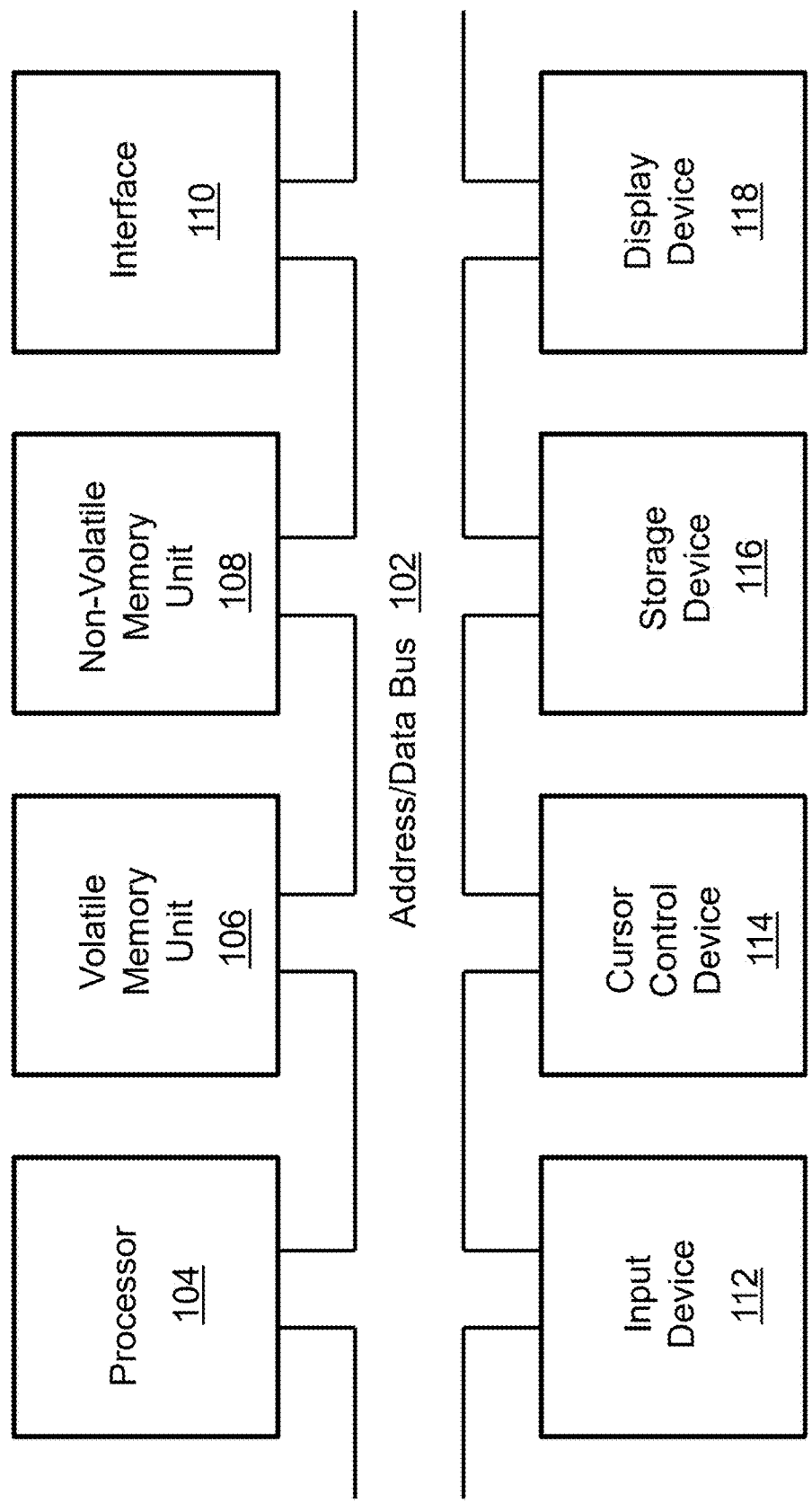
FIG. 1 is a block diagram depicting the components of a system for personalizing a human-machine interface (HMI) device according to some embodiments of the present disclosure.

The present invention relates to system for personalizing a human-machine interface device, and more particularly, to a system for personalizing a human-machine interface device that utilizes bio-signals from a user for its adaptation to the user. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Borghini, F. (2017). EEG-based cognitive control behaviour assessment: an ecological study with professional air traffic controllers. Nature. Scientific Reports, 7: 547.
2. Findlater and McGrenere (2004). A comparison of static, adaptive, and adaptable menus, CHI '04 Proceedings of the SIGCHI Conference on Human Factors in Computing Systems.
3. Benson, J. (2015). Natick scientists investigate ways to help soldiers recover from stress. Natick Soldier Research, Development and Engineering Center (NSRDEC) Public Affairs.
4. Lebedev, M. (2011). Future developments in brain-machine interface research. Clinics (Sao Paulo), 66(Suppl 1): 25-32.
5. Luque-Casado, A., Zabala, M., Morales, E., Mateo-March, M., Sanabria, D. (2013). Cognitive Performance and Heart Rate Variability: The Influence of Fitness Level. PLoS ONE, 8(2).
6. Hogervorst, M. A., Brouwer, A. M. and van Erp, J. B. F. (2014). Combining and comparing EEG, peripheral physiology and eye-related measures for the assessment of mental workload. Front. Neurosci.
7. Picard, R. W. Detecting seizures and their autonomic impact with a wristband.
8. Optimizing Human-Automation Team Workload through a Non-Invasive Detection System. DARPA—Office of the Under Secretary of Defense for Acquisition.
9. IARPA—Using Neural Tools to Augment Prediction of Performance, Expertise, and Domain-knowledge.
10. Marcora, Staiano, and Manning V. (2008). Mental fatigue impairs physical performance in humans. Journal of Applied Physiology Published 1 Mar. 2009, Vol. 106 no. 3, 857-864.
11. Yang, Fang, Sun, Siemionow, et al. (2009). Weakening of Functional Corticomuscular Coupling during Muscle Fatigue. Brain Res., 1250: 101-112.
12. Zimmer, H. (2002). Habituation and recovery of a slow negative wave of the event-related brain potential. International Journal of Psychophysiology, vol. 43, pp. 225-235, 2002.
13. Gawron, V. J. (2000). Human performance measures handbook. Mahwah, N.J., US: Lawrence Erlbaum Associates Publishers.
14. Chandra, Verma, Sharma, Mittal, and Jha (2015). EEG based cognitive workload classification during NASA MATB-II multitasking. International Journal of Cognitive Research in Science, Engineering and Education. Vol. 3, No. 1.
15. Bossard, Kermarrec, Buche, and Tisseau (2008). Transfer of learning in virtual environments: a new challenge? Virtual Reality, Volume 12, Issue 3, 151-161.
16. Mohammad-Rezazadeh, Firoozabadi, Hashemi, Hu (2011). A Novel Human-Machine Interface based on Recognition of Multi-Channel Facial Bioelectric Signals. Australas Phys Eng Sci Med, 34:497-513.
17. Mohammad-Rezazadeh, Firoozabadi, Hu, Hashemi Golpayegani (2012). Co-Adaptive and Affective Human-Machine Interface for Improving Training Performances of Virtual Myoelectric Forearm Prosthesis. IEEE Transactions on Affective Computing, Vol 3: 285-297.
18. Castanedo, F. (2013). A Review of Data Fusion Techniques. The Scientific World Journal. Volume 2013, Article ID 704504.
19. Fallahi, M., Heidarimoghadam, R., Motamedzade, M., Farhadian, M. (2016). Psycho Physiological and Subjective Responses to Mental Workload Levels during N-Back Task. J Ergonomics, 6:181.
20. Kolouri, S., Park, S., Thorpe, M., Slepcev, D. and Rohde, G. K. (2017). Optimal Mass Transport: Signal Processing and Machine-Learning Applications. IEEE Signal Process Mag., 34(4):43-59.
21. Kumar, N., Kumar J. (2016). Measurement of Cognitive Load in HCl Systems Using EEG Power Spectrum: An Experimental Study. Procedia Computer Science, 84: 70-78.

(2) Principal Aspects

Various embodiments of the invention include three "principal" aspects. The first is a system for personalizing a human-machine interface device. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
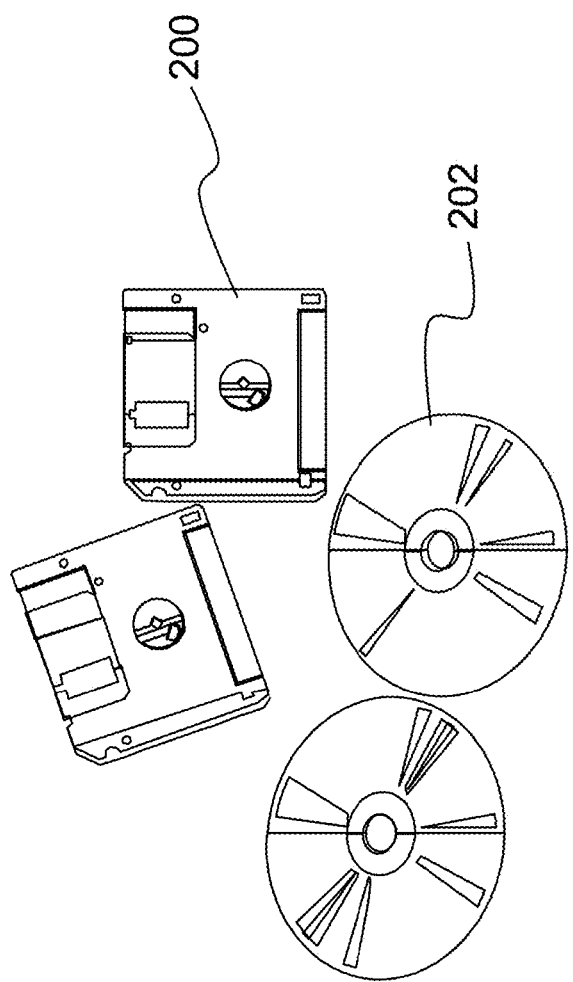
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e.

computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is an electroencephalography (EEG)-free and neuro-adaptive human-in-the-loop system utilizing a Universal Mental-State Model (UM2) to improve the interaction quality, performance, and collaboration between human and machine. The developed model is personalized to each individual user and can be deployed in a fielded application for continuous adaptation of the machine to its user's mental states. This real-time adaptation will, consequently, reduce the user's mental/physical workloads (i.e., efforts).

Figure 3:
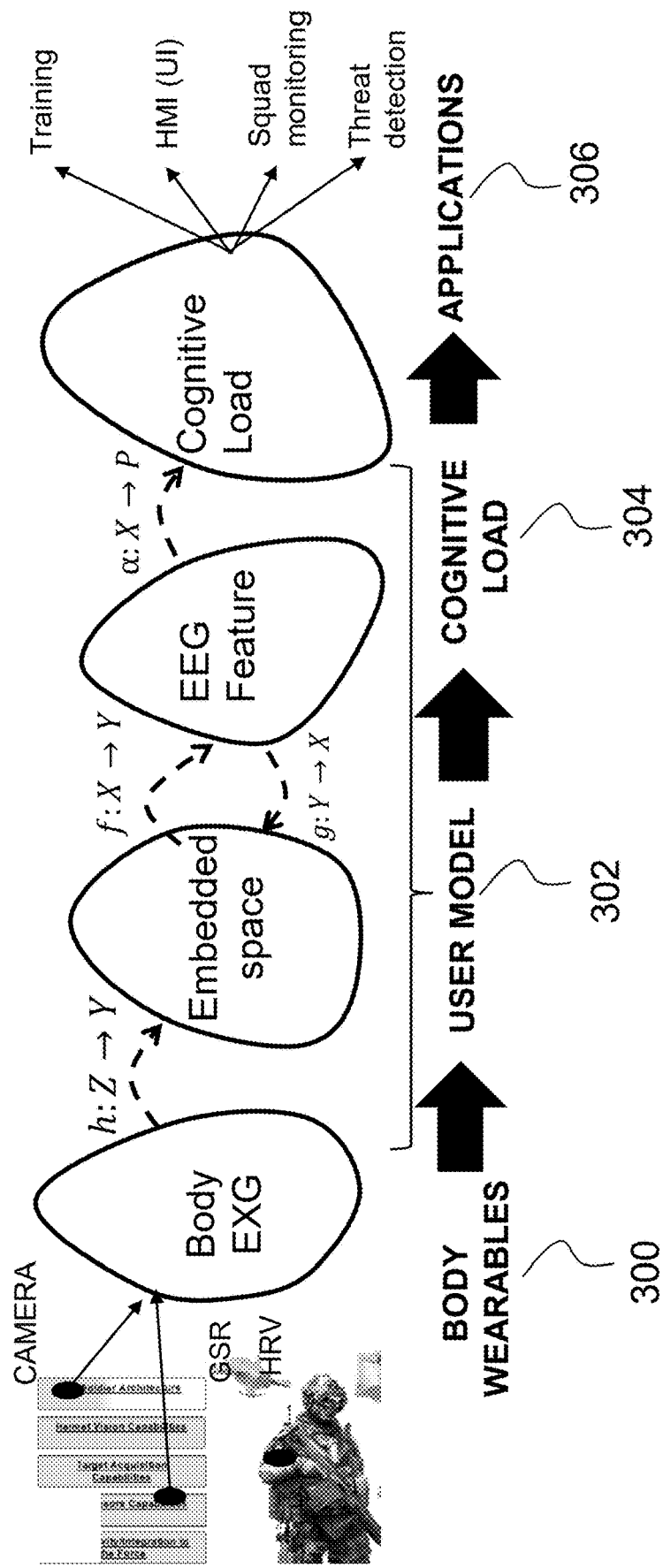
FIG. 3 is an illustration of the flow of information in the system for personalizing a HMI device according to some embodiments of the present disclosure.

Physical and cognitive readiness are interdependent. FIG. 3 illustrates the flow of information in the system for personalizing a HMI device according to embodiments of the present disclosure. Sensor data is obtained from body wearables (element 300) to determining a user model (element 302). The user model (element 302) is used to generate an estimation of cognitive load (element 304), which is utilized in applications (element 306) in fields, such as training, human-machine interfaces (HMIs), user and group monitoring, and threat detection. Input signals (e.g., GSR, HRV, EKG, Video) will be recorded in the Z domain and transferred to the Y domain, which is a rich space in terms of information value. Then, another mapping is performed to map Y to a single variable (electrocardiogram (EKG, for example). The g function is an inverse of the f function. The a function is used to map the single variable (e.g., EKG) to cognitive load, which can be used in variety of application such as training, HMI, squad monitoring, and threat detection.

Cognitive load (element 304) can be estimated using robust body sensing via sensors (element 300), such as galvanic skin response (GSR) sensors and heart rate variability (HRV) sensors. The system described herein is a unique approach to cognitive load prediction (element 304) with a personalized user model (element 302) that is context-independent and EEG-free, yet based on neural signatures. Deployment of the personalized user model (element 302) in a fielded application (element 306) continuously adapts the HMI to its user's mental and physical states to reduce workload and enhance decision making. Non-limiting examples of benefits include assessing user (e.g., soldier, pilot, amputee, disabled person) readiness and improving the interaction quality, performance, and collaboration in real world applications and between the user and human/machine counterpart(s).

Figure 4:
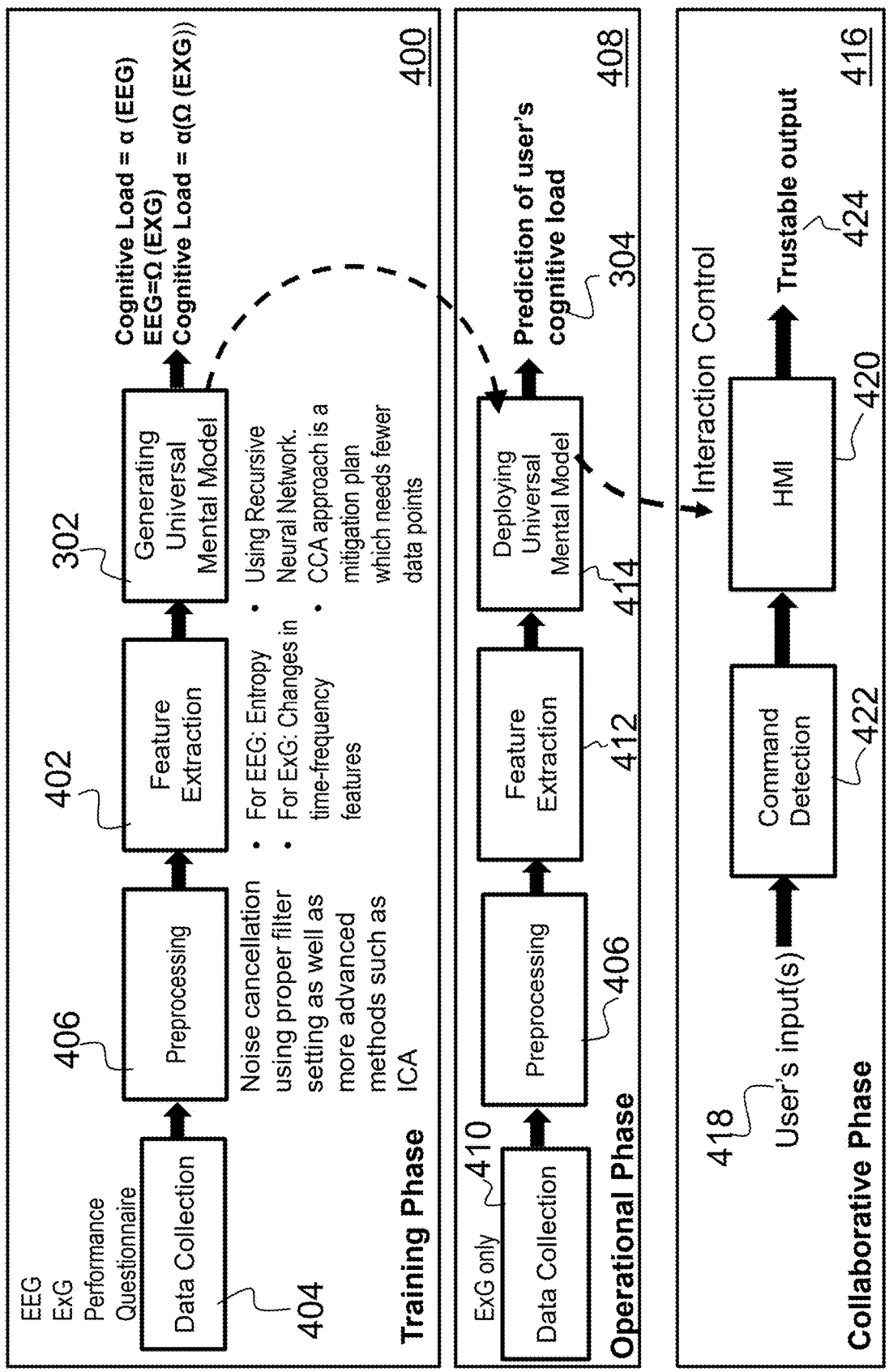
FIG. 4 is an illustration of a training phase, an operational phase, and a collaborative phase for personalizing a human-machine interface according to some embodiments of the present disclosure.

As described above, the method described herein generates a universal mental state model (element 302) utilizing the fusion of subjective data (e.g., amplitude of EEG, amplitude of GSR) as well as environmental sensors (element 300) (e.g., cameras, microphones (audio), thermometers (temperature)) in a training phase (element 400), as shown in FIG. 4. Data from the environmental sensors (element 300) can be fused with the subjective data using either a relationship based method or an abstraction based method, such as that described in Literature Reference No. 18.

For each user, basic and context-independent principal cognitive components (or features) are examined during feature extraction (element 402) while the subjective data and environmental sensors are recorded (see Literature Reference No. 19). For EEG data, features related to entropy can be extracted, while changes in time-frequency features can be extracted for ExG sensors. EEG entropy quantifies an amount of uncertainty or randomness in the EEG pattern. Using advanced machine learning methods (see Literature Reference No. 20), a relationship between the collected multi-resolution signals is identified to develop the context-independent user cognitive model (element 302). In short, the method consists of a training and a testing phase. In the training phase, the method uses high resolution data and morphs it to template high-resolution data through optimal transport maps. Next, the system learns a subspace for the calculated optimal transport maps. A transport map in this subspace can then be applied to the template data to synthesize high-resolution data. In the testing phase, the goal is to reconstruct a high-resolution data from the low-resolution input data. The method searches for a synthetic high-resolution data (generated from the transport subspace) that provides a corresponding low-resolution data which is similar to the input low-resolution data.

During data collection (element 404) in the training phase (element 400), the user's cognitive capabilities are examined using principal cognitive tests, such as performance questionnaires, EEG, and ExG (such as GSR and HRV). In addition, the training can be more focused to a specific task by performing the training on the task. EEG has shown to be a reliable identifier of human's cognitive state/load. Therefore, during data collection (element 404), EEG, cognitive state dependent biological signals (ExG: GSR and HRV), and task performance information are collected while testing users. Pre-processing (element 406) of the data collected may be necessary. For instance, noise cancellation using proper filter settings as well as more advanced methods, such as ICA (independent component analysis), can be utilized.

In generation of the universal mental model (element 302) and during machine (or transfer) learning, a recursive neural network (RNN) is generated to learn the temporal transfer function (function $f$ in FIG. 3) between extracted features from EEG and ExG. A RNN is a deep neural network created by applying the same set of weights recursively over a structured input to generate a structured prediction over variable-size input structures, or a scalar prediction on it, by transversing a given structure in topological order. In the transfer learning approach, instead of random weights, allocation weights are set using all of the already collected datasets. Later, the model will be refined or fine-tuned using data for an individual user (personalized model (element 302)). If the action/context detection is necessary, then an unsupervised context detection approach will be utilized. An example of an unsupervised context detection approach is detecting if an operation is done in the day or night based on lighting condition changes.

In an operational phase (element 408), EEG sensors will be detached from the user, and the user's profile (i.e., mental states) can be deduced from data collection (element 410) using the remaining sensors in a fielded operation (i.e., ExG). A cognitive basis set of tasks from feature extraction (element 412) is developed that deploys a universal mental model (UM2) (element 414) capable of prediction of 1) cognitive load (element 304), and 2) task performance in real world applications (element 306). The new features (element 412) in the operational phase (element 408) are used to adapt the UM2 (element 414). Performance will vary according to task dimensions, including mental and physical effort, frustration, task difficulty, and temporal dynamics. In a collaborative phase (element 416), a user's inputs (element 418) can be translated into commands for an HMI (element 420), which are detected through command detection (element 422), and a trustable output (element 424) is generated. For instance, an HMI (e.g., robot) can be commanded to move forward with a joystick. The HMI can include motion sensors, keyboards, speech-recognition interfaces, touch-screens, and any other machine component that allows information (e.g., sight, sound, heat) to be exchanged between a human user and a machine. For example, data can be displayed to the user in a graphical format through a graphical user interface (GUI).

Because of rich information content in the UM2 approach, any HMI (element 420) which utilizes a neuro-adaptive body sensing for user states (NABSUS) framework is able to detect and track a user's state continuously. Additionally, an HMI (element 420) utilizing NABSUS can detect abrupt variations in the interaction between the user and the HMI (element 420), such as existing noise in the system (i.e., noisy environment). The NABSUS framework provides a personalized UM2 by continuously adapting to users' previous experiences, changes in skill level, an extent of distraction, mental traits, and physical state, such as fatigue. By understanding the user's state, the HMI tries to increase/decrease its interaction in order to increase the overall task performance. This unique neuro-adaptive approach will substantially leverage the context awareness and skill of partnering humans and machine for future autonomous systems, because it has been shown that users don't trust over simplified HMIs.

Figure 5:
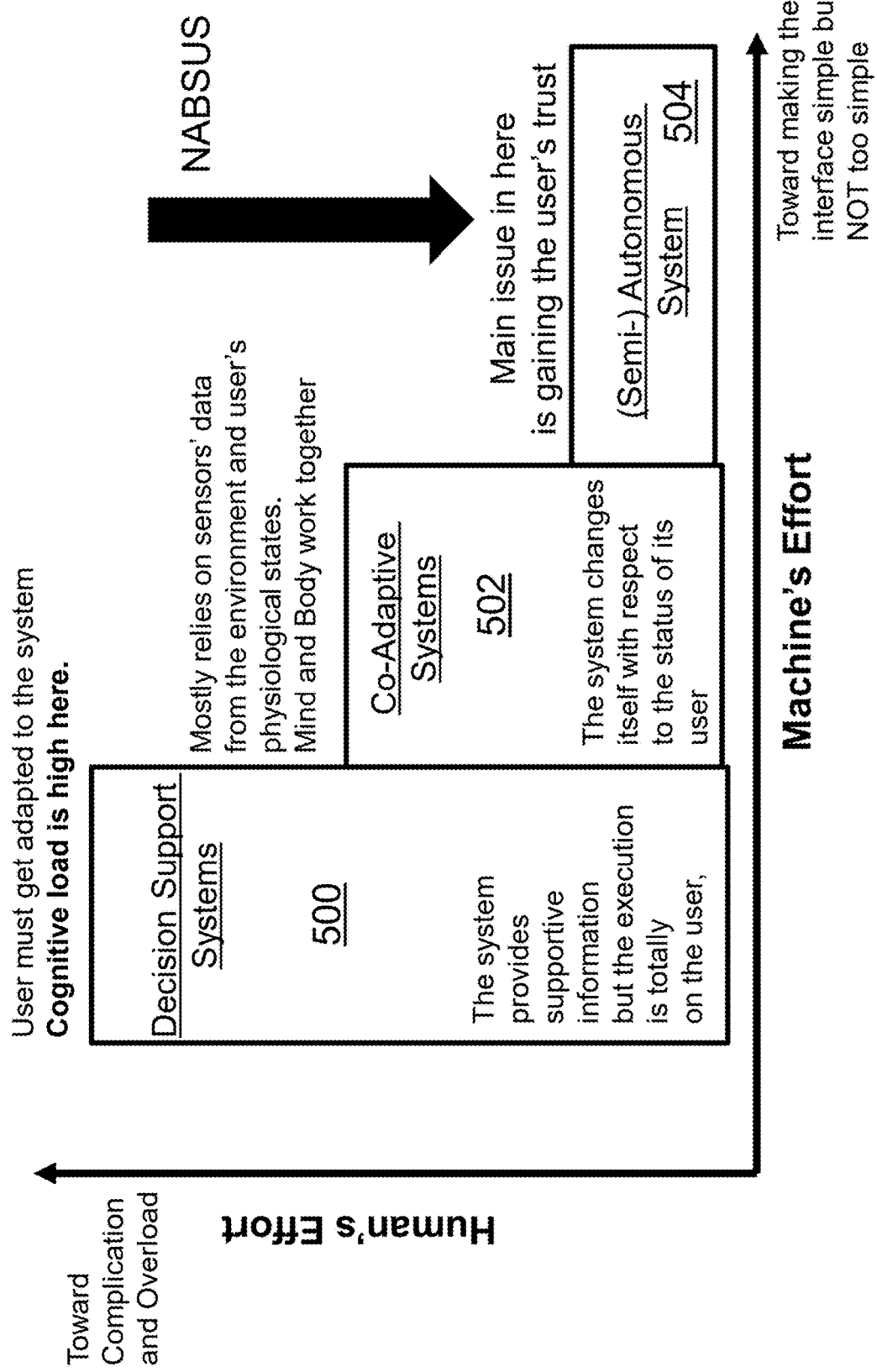
FIG. 5 is an illustration of the neuro-adaptive body sensing for user states (NABSUS) framework according to some embodiments of the present disclosure.

FIG. 5 illustrates a diagram comparing a machine's effort and human's effort. A human's effort increases towards complication and cognitive overload. Similarly, a machine's effort increases towards making the interface simple but not too simple. Decision support systems (element 500) provide supportive information. Examples of decision support systems (element 500) include systems which can help users to make better judgment under various situations. For example, if the user is under a lot of stress, then it is a possibility to make more mistakes. Now, the HMI can interact with the user and prompt him about his "irrational" decision.

The user must get adapted to the system, but the execution is entirely on the user, such that cognitive load is high. Co-adaptive systems (element 502) rely mostly on sensors' data from the environment and the user's physiological states, such that mind and body work together. The system changes itself with respect to the status of its user. Finally, in a (semi-) autonomous systems (element 504), which is the target of NABSUS, the main issue is gaining the user's trust. Trust, or believing that HMIs will do what they were designed to do, is critical to deriving the most value from autonomous systems. Autonomous systems are vital in terms of untapped efficiency and effectiveness, for a host of new applications in domains such as health, defense, aviation, and agriculture. Many companies are propelling the technology boom by developing or investing in the most advanced robots and autonomous systems. However, the most advanced technologies will not matter if humans do not adopt, trust, or feel comfortable using them. For example, people treat separate computers as individual entities in a social context, even while admitting that they assume only one programmer is behind them both. This finding was extended to assume that participants might treat separate artificial intelligence (AI) software versions with different names as individual entities.

Figure 6:
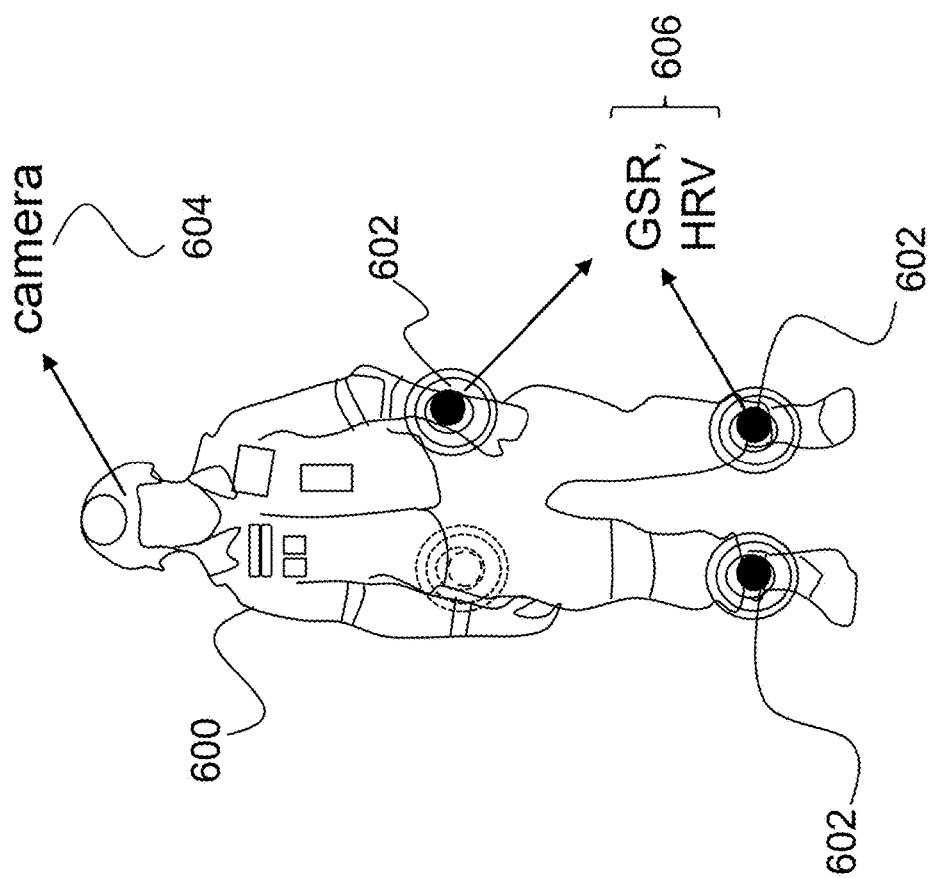
FIG. 6 is an illustration of a user with wearable sensors attached to obtain necessary biological signals according to some embodiments of the present disclosure.

FIG. 6 depicts a user (element 600) wearing commercially available sensors (element 602) and a camera (element 604). The camera (element 604) is used to help understand users' motions, facial gestures, and, in general, the context. Depending on the application of the HMI, the type of camera may be changed (e.g., night vision camera). During training for each user (element 600), biological signals (element 606) related to the user's state including, EEG, electrocardiogram (ECG), and GSR are recorded using the wearable sensors (element 602) while the user (element 600) is performing a task in a virtual reality simulation environment, such as driving a car, piloting an aircraft, or sniper training. These biological signals are captured in the data collection stage (element 404), shown in FIG. 4. The task performance metrics (such as completion time, accuracy, trajectory smoothness), environmental conditions (such as darkness level, air condition), and user's self-/supervisory reports (e.g., NASA TLX) can also be measured during performing the task. Then, important biometric features (extracted through feature extraction (element 412)) related to a user's mental effort (e.g., brain entropy in alpha and beta bands (see Literature Reference Nos. 15 and 16) and physical status (e.g., muscular fatigue by extracting spectrogram of EMG) will be extracted to determine a user's state.

Figure 7:
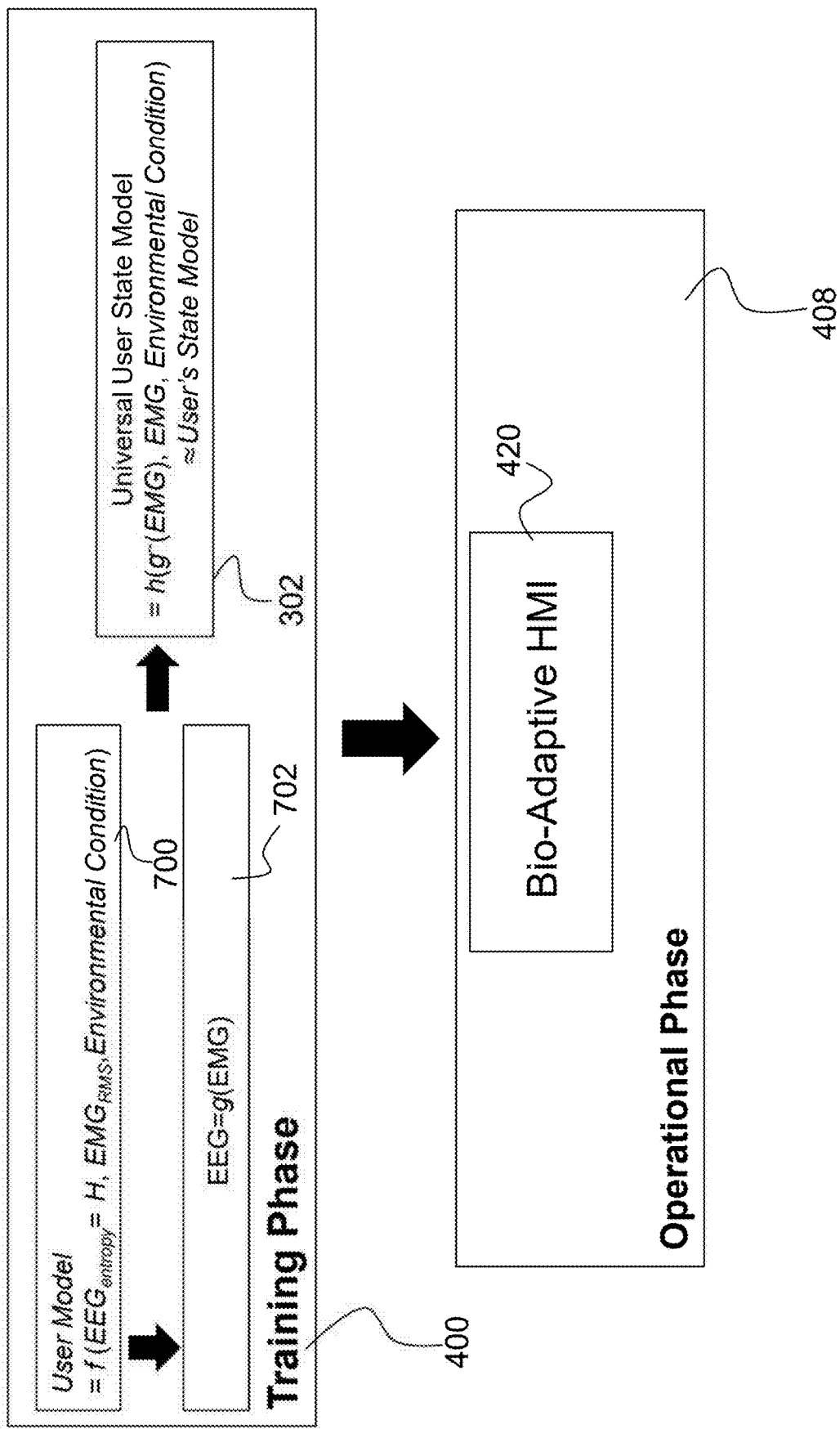
FIG. 7 is an illustration of a universal user state model during training and its use in the operational phase according to some embodiments of the present disclosure.

FIG. 7 is a block diagram illustrating the training phase (element 400) and the operational phase (element 408). In the training phase (element 400), a user model (element 700) is determined according to the following:

User Model=$f$(EEG$_{entropy}$=entropy=$H$,EMG$_{RMS}$,Environmental Condition), where EMG$_{RMS}$=$\sqrt{\sum EMG_t^2/T}$, $H_{LogEn}$=$-\Sigma_{t=0}^{N-1}(\log_2(P_i(x))^2$, where T denotes time period of recording, N denotes the number of samples in each calculation, and $P_i$ denotes a probability density function of X.

Afterward, using a Generalized Linear Model (GLM) (element 702), EEG entropy will be correlated with biometric data (EMG$_{RMS}$) as well as performance metrics to generate a personalized and universal user model (element 302) as follows:

EEG=GLM(EMG); Y=EEG and X=EMG $E(Y)$=$g^{-1}(XB)$

Var($Y$)=$V(g^{-1}(XB))$, where B represents a weighting matrix, g is the inverse of the f function in FIG. 3, V denotes variance, and E is an expected value. The model is initially universal, meaning the model can be used by every user, and over time becomes personalized as it adapts to a specific user. By employing a thresholding method which is sensitive to the changes of the user's state (first derivation of the entropy; if V(Y)>threshold), the obtained model (element 302) can predict/track a user's mental state based on his/her current state. In other words, if the user is stressed the entropy is high and above a certain threshold. In the operational phase (element 408), a bio-adaptive human machine interface (HMI) (element 420) according to embodiments of the present disclosure utilizes the extracted bio-signals/states for its adaptation to the user and current context (e.g., task difficulty, time of the task, number of teammates).

Figure 8:
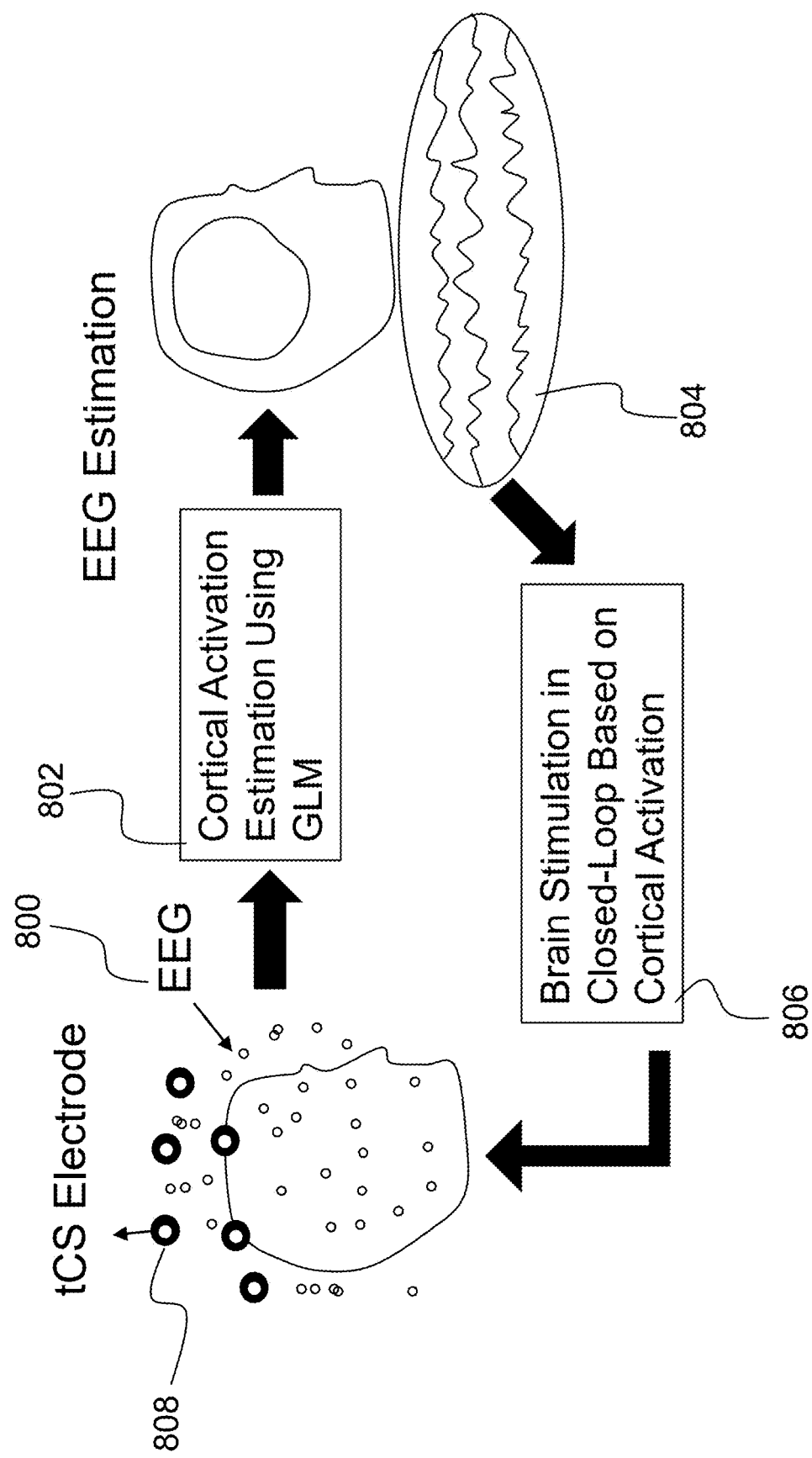
FIG. 8 is an illustration of a closed-loop system in operation according to some embodiments of the present disclosure.

FIG. 8 illustrates a block diagram of the closed-loop system described herein in operation. Using EEG data (element 800) from the user and the GLM (element 702), a cortical activation estimation (element 802) of EEG data (element 804) is performed. Based on the cortical activation, brain stimulation (element 806) is applied via electrodes (e.g., tCS electrode (element 808)) positioned on the user's scalp. The system provides adequate transcranial stimulation (tCS) (transcranial direct current stimulation (tDCS)/transcranial alternating current stimulation (tACS)) neurostimulation feedback to its user to apply necessary changes in the human-in-the-loop system and, consequently, maintain or boost performance metrics. Then, EEG data (element 800) can be obtained again from the user after application of the brain stimulation (element 806).

Figure 12:
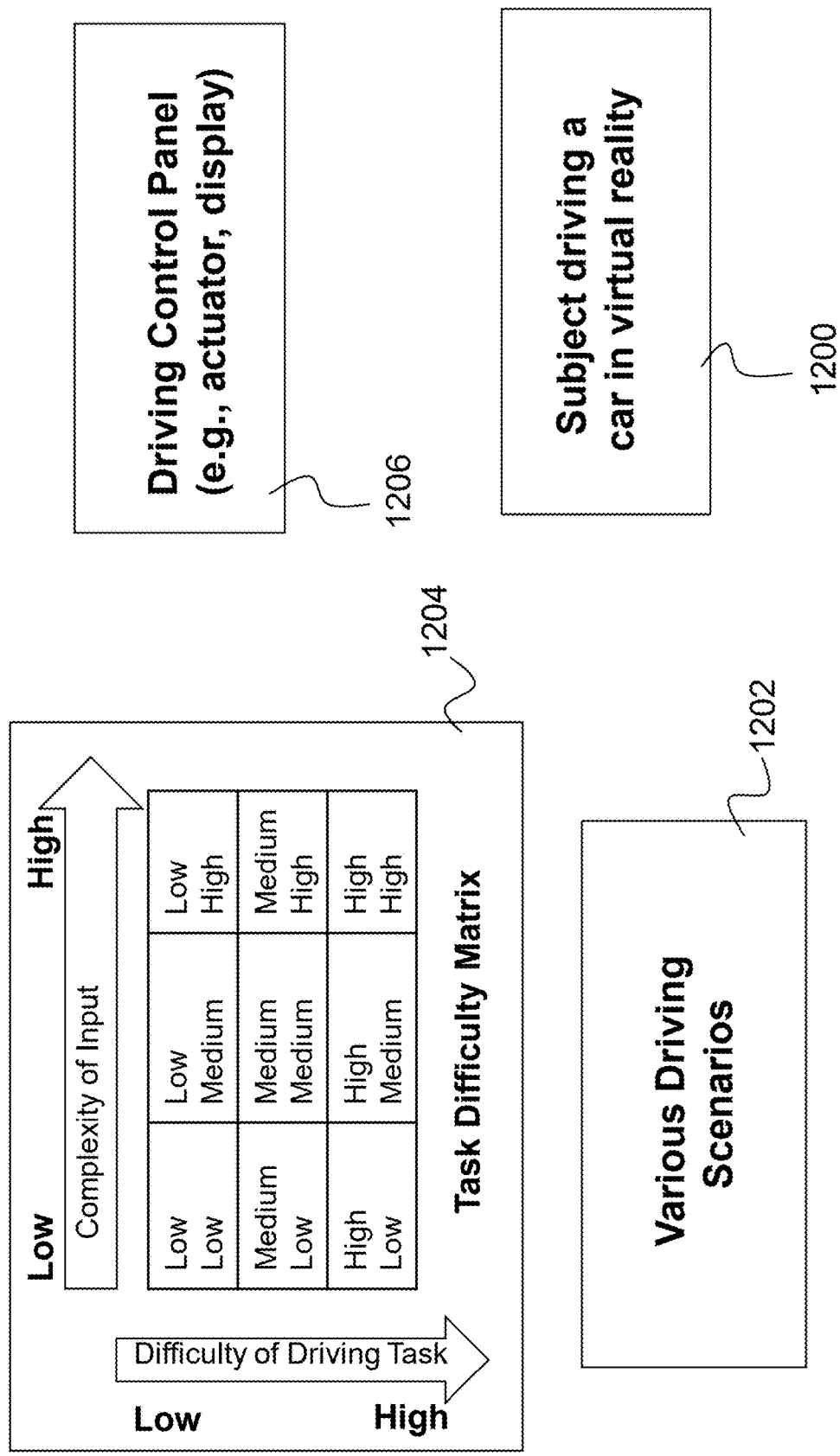
FIG. 12 is an illustration of an experimental design setup and protocol according to some embodiments of the present disclosure.

FIGS. 9-11 are tables describing prior art methods, their limitations, and comparisons to the system and method described herein. To validate the efficacy of the system and method according to embodiments of the present disclosure, the overall performance of the NAB SUS framework's was compared to non-adaptive and non-predictive HMI prior art approaches in which either no or very simple feedback is provided to users. FIG. 12 shows an experimental design setup and protocol. The approach according to embodiments of the present disclosure has been developed and examined under the aim to identify a universal mental-state model (element 302), which can discriminate cognitive abilities of different users. At this preliminary/exploratory study, EEG data was collected from nine subjects driving a car in virtual reality (element 1200) while performing a dual 1) driving and 2) procedural task in the virtual reality driving simulation of various driving scenarios (element 1202).

In one embodiment, three levels of difficulty for both 1 and 2 were designed, resulting in nine difficulty levels, as depicted in the task difficulty matrix (element 1204). Once the driving task began, participants were first given an opportunity to drive without a goal within the simulation space to become familiar with the controls of the vehicle (i.e., driving control panel 1206). Next, participants were asked to drive five laps on a circuit track with several obstacles (i.e., various driving scenarios (element 1202)). As the driving task difficulty level increases, the visibility is decreased, lane width is decreased, more difficult tracks contain sharp turns, and the behavior of obstacles becomes less predictable. Difficulty for the procedural task was increased by asking the participant to input an increasingly complex sequence of buttons when they see a specific type of actor (e.g., cyclists, pedestrians, motorized vehicles) moving on the display screen of the driving control panel (element 1206), as outlined in the task difficulty matrix (element 1204). After each scenario, the subject was asked to complete a questionnaire (e.g., NASA TLX questionnaire), where users rated their own performance. The entropy of the EEG signal in the alpha frequency range and at the occipital region of the brain (see Literature Reference No. 21) was extracted in each 256 milliseconds (ms) time slot.

Figure 13:
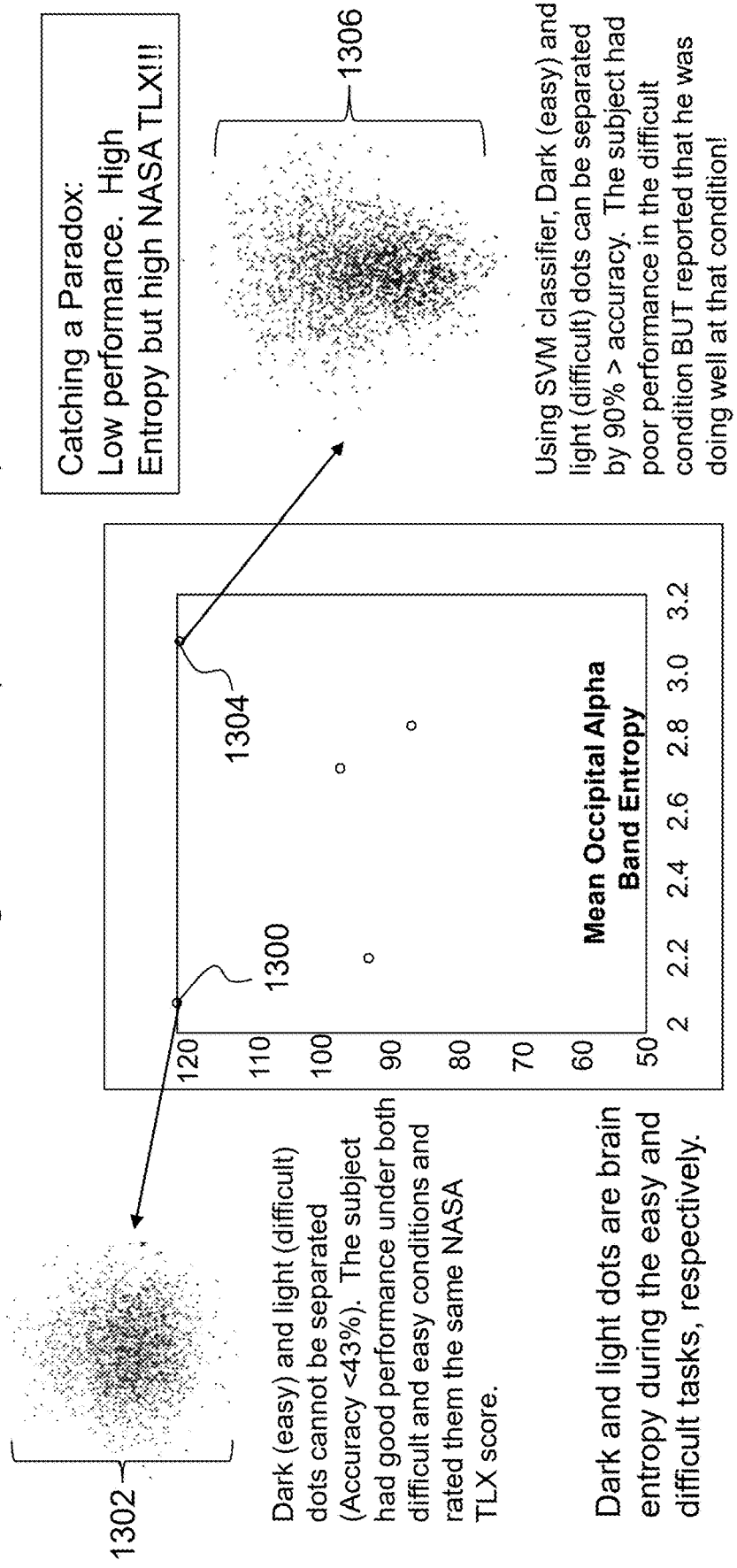
FIG. 13 is an illustration of results of a study showing the capability of the NAB SUS framework to detect user's mental state and predict physical performance according to some embodiments of the present disclosure.

The results of the invention described, depicted in FIG. 13, showed that the brain entropy can discriminate different mental workloads needed to perform a task in different difficulty levels. However, the results of a self-report questionnaire can be misleading as users may be biased and not always rate their performance properly. Each circle in the center plot shows the average brain entropy (x-axis) as well as NASA TLX score (y-axis) for a participant. The circle 1300 can be extrapolated to the cluster 1302 of dark and light dots. Dark dots represent brain entropy during easy tasks and light dots represent brain entropy during difficult tasks. In the cluster 1302, dark and light dots could not be separated (accuracy <43%). The subject had good performance (i.e., low entropy) under both difficult and easy conditions and rated them the same NASA TLX score. In a different data point, the circle 1304 was extrapolated to the cluster 1306. The circle 1304 indicates that the subject rated both difficult and easy conditions with a high NASA TLX score. However, the performance was low, as indicated by the high entropy value. Thus, the NASA TLX score alone would not be able to distinguish between different mental workloads, since the subject rated them the same. The cluster 1306 shows separation of the dark and light dots (brain entropy during easy and difficult tasks, respectively), indicating that brain entropy can discriminate different conditions needed to perform a task in different difficulty levels.

The NAB SUS framework described herein provides efficient methods of interaction in human-in-the-loop systems by utilizing several unique aspects, as described above. Biomarkers (or biosignals) on brain activities are extracted during task performance using brain entropy measures in broadband and a specific frequency domain (such as but not limited to Alpha). EEG signals/features are fused with other related physiological signals such as, but not limited to, EKG, EMG, and GSR. Additionally, the system can identify a correlation between extracted biomarkers and performance indices using multivariate analysis approaches, such as a generalized linear model. The invention described herein can be applied in a variety of applications such as a performance predictor to estimate the temporal sequence of a user's cognitive state (i.e., mental load or disorientation) in new situations (e.g., in flight simulators) and personalize a training environment based on the user's model.

Additionally, the system according to embodiments of the present disclosure can be applied to usability evaluation of new designs to examine how a new design/settings in an interface (e.g., plane cockpit, car's interior) or widgets may have an effect on users' performance. This neuro-ergonomic application can eliminate unnecessary modifications in interfaces and make designs more user-centered and customized to the real needs of users.

The system can also be applied as a mental breakdown predictor to develop a human-based warning/assistive computational model which predicts future cognitive performance as well as the maximum level of cognitive strain (such as fatigue and loss of situation awareness (i.e., performance changes) that a user can cope with and prevent accidents caused by mental break-down. Furthermore, the invention can be applied as a closed-loop re-engagement to design closed-loop brain stimulation techniques which can deliver non-invasive stimulus (i.e., tCS) to reorient operators and bring them back to a "mentally safe zone" from the breakdown zone.

The approach described herein can provide important information for detection of emergencies due to the lack of concentration, drowsiness, or too high of mental pressure in safety-critical applications, such as driving or security surveillance, spatial disorientation monitoring, and semi-autonomous vehicles in the automobile industry. In these situations, an alert can be automatically generated by the system. The alert can be a visual alert on a display, an auditory alert, a vibratory alert, or any suitable type of alert to cause the user to become more alert/awake. Furthermore, if lack of concentration or drowsiness is detected, the system can cause an autonomous vehicle to perform an operation, such as stopping (through a braking operation), decreasing speed, or changing a position of the autonomous vehicle.

In addition, the system and method described herein creates an enabling technology for the design process for interfaces in autonomous systems, which are useful for aircraft, automobiles, and many other platforms. For instance, the interface can be used to detect how the passenger feels and adjust the speed and/or position of the autonomous vehicle accordingly.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for personalizing a human-machine interface (HMI) device, the system comprising:
   one or more processors and a non-transitory memory having instructions encoded thereon such that when the instructions are executed, the one or more processors perform operations of:
   during performance of a task in a simulation environment,
      extracting a first set of biometric features from data collected from one or more body sensors; and
      extracting a set of brain entropy features from electroencephalogram (EEG) signals;
   correlating the set of brain entropy features with the first set of biometric features, resulting in a correlation of features;
   generating a mental-state model as a function of the correlation of features, where in generating the mental-state model, the set of brain entropy features are further correlated with a set of performance metrics, wherein the set of performance metrics are obtained during the task performance in the simulation environment; and
   deploying the mental-state model in an HMI device during performance of the task in an operational environment for continuous adaptation of the HMI device.

2. The system as set forth in claim 1, wherein during performance of the task in the operational environment, the deployed mental-state model is used to predict a mental state.

3. The system as set forth in claim 1, where in generating the mental-state model, the set of brain entropy features are further correlated with a set of environmental condition features.

4. The system as set forth in claim 1, wherein the one or more processors further perform an operation of translating human inputs into commands for the HMI deploying the mental-state model.

5. The system as set forth in claim 1, wherein during performance of the task in the operational environment, the one or more processors perform operations of:
extracting a second set of biometric features from data collected from the one or more body sensors; and
refining the deployed mental-state model with the second set of biometric features, resulting in a refined mental-state model.

6. The system as set forth in claim 5, wherein the one or more processors further perform an operation of controlling application of neurostimulation during performance of the task in the operational environment based on the refined mental-state model.

7. A computer implemented method for personalizing a human-machine interface (HMI) device, the method comprising an act of:
causing one or more processors to execute instructions encoded on a non-transitory computer-readable medium, such that upon execution, the one or more processors perform operations of:
during performance of a task in a simulation environment,
extracting a first set of biometric features from data collected from one or more body sensors; and
extracting a set of brain entropy features from electroencephalogram (EEG) signals;
correlating the set of brain entropy features with the first set of biometric features, resulting in a correlation of features;
generating a mental-state model as a function of the correlation of features, where in generating the mental-state model, the set of brain entropy features are further correlated with a set of performance metrics, wherein the set of performance metrics are obtained during the task performance in the simulation environment; and
deploying the mental-state model in a HMI device during performance of the task in an operational environment for continuous adaptation of the HMI device.

8. The method as set forth in claim 7, wherein during performance of the task in the operational environment, the deployed mental-state model is used to predict a mental state.

9. The method as set forth in claim 7, where in generating the mental-state model, the set of brain entropy features are further correlated with a set of environmental condition features.

10. The method as set forth in claim 7, wherein the one or more processors further perform an operation of translating human inputs into commands for the HMI deploying the mental-state model.

11. The method as set forth in claim 7, wherein during performance of the task in the operational environment, the one or more processors perform operations of:
extracting a second set of biometric features from data collected from the one or more body sensors; and
refining the deployed mental-state model with the second set of biometric features, resulting in a refined mental-state model.

12. The method as set forth in claim 11, wherein the one or more processors further perform an operation of controlling application of neurostimulation during performance of the task in the operational environment based on the refined mental-state model.

13. A computer program product for personalizing a human-machine interface (HMI) device, the computer program product comprising:
computer-readable instructions stored on a non-transitory computer-readable medium that are executable by a computer having one or more processors for causing the processor to perform operations of:
during performance of a task in a simulation environment,
extracting a first set of biometric features from data collected from one or more body sensors; and
extracting a set of brain entropy features from electroencephalogram (EEG) signals;
correlating the set of brain entropy features with the first set of biometric features, resulting in a correlation of features;
generating a mental-state model as a function of the correlation of features, where in generating the mental-state model, the set of brain entropy features are further correlated with a set of performance metrics, wherein the set of performance metrics are obtained during the task performance in the simulation environment; and
deploying the mental-state model in a HMI device during performance of the task in an operational environment for continuous adaptation of the HMI device.

14. The computer program product as set forth in claim 13, wherein during performance of the task in the operational environment, the deployed mental-state model is used to predict a mental state.

15. The computer program product as set forth in claim 13, where in generating the mental-state model, the set of brain entropy features are further correlated with a set of environmental condition features.

16. The computer program product as set forth in claim 13, wherein during performance of the task in the operational environment, the one or more processors perform operations of:
extracting a second set of biometric features from data collected from the one or more body sensors; and
refining the deployed mental-state model with the second set of biometric features, resulting in a refined mental-state model.

17. The computer program product as set forth in claim 16, wherein the one or more processors further perform an operation of controlling application of neurostimulation during performance of the task in the operational environment based on the refined mental-state model.

* * * * *